United States Patent [19]

Kurihara et al.

[11] Patent Number: 5,242,693
[45] Date of Patent: Sep. 7, 1993

[54] PROTEIN CURUCULIN AND APPLICATION OF THE SAME

[75] Inventors: Yoshie Kurihara, 4-7, Okuzawa 7-chome, Setagaya-ku, Tokyo 125, Japan; Hiroshige Kohno; Masaaki Kato; Kenji Ikeda; Masako Miyake, all of Tokyo, Japan

[73] Assignees: Yoshie Kurihara; Asahi Denka Kogyo Kabushiki Kaisha, both of Tokyo, Japan

[21] Appl. No.: 655,184

[22] Filed: Feb. 13, 1991

Related U.S. Application Data

[63] Continuation of Ser. No. 362,857, Jun. 7, 1989, abandoned.

[30] Foreign Application Priority Data

| Jun. 21, 1988 | [JP] | Japan | 63-153143 |
| Nov. 2, 1988 | [JP] | Japan | 63-277717 |
| Nov. 2, 1988 | [JP] | Japan | 63-277718 |
| Nov. 2, 1988 | [JP] | Japan | 63-277719 |
| Nov. 2, 1988 | [JP] | Japan | 63-277720 |

[51] Int. Cl.⁵ .......................................... A23L 1/221
[52] U.S. Cl. .............................. 426/3; 426/548; 426/615; 426/650; 426/534; 426/655; 426/627; 426/640; 530/370; 424/50; 424/58
[58] Field of Search .............. 426/548, 615, 650, 534, 426/655, 627, 648, 3; 530/370; 424/50, 58

[56] References Cited

U.S. PATENT DOCUMENTS 3,682,880 8/1972 Brouwer et al. ............... 426/548 X

Primary Examiner—Joseph Golian
Attorney, Agent, or Firm—Frishauf, Holtz, Goodman & Woodward

[57] ABSTRACT

A protein curuculin obtained by extracting from fresh Curculigo latifolia fruits or dried fruits thereof with an aqueous solution of a salt of a concentration of at least 0.01M; a taste-modifier for a sour material comprising fresh Curculigo latifolia fruits, dried fruits thereof or a curuculin-containing material obtained therefrom; a chewing gum composition comprising fresh Curculigo latifolia fruits, dried fruits thereof or a curuculin-containing material obtained therefrom; and a mouth-wash composition comprising fresh Curculigo latifolia fruits, dried fruits thereof or curuculin-containing material obtained therefrom are disclosed.

11 Claims, No Drawings

PROTEIN CURUCULIN AND APPLICATION OF THE SAME

This application is a continuation of application Ser. No. 07/362,857, filed Jun. 7, 1989 (abandoned).

BACKGROUND OF THE INVENTION

1. Field of the Invention

This invention relates to a novel protein curuculin and the application of the same as a taste-modifier. Curuculin is a coined word.

2. Description of the Prior Art

Known taste-modifiers, which affect the receptor membranes on the tongue in such a manner as to modify the taste of a food, include those which remove the sweetness of a sweet food in the mouth, for example, gymnemic acid contained in Gymnema sylvestre leaves and ziziphine contained in Ziziphus jujuba leaves; and those which convert the sourness of a sour food into sweetness in the mouth, for example miraculin contained in Synsepulm dulcificum fruits.

Japanese Patent Publication No. 32068/1974 discloses an example of the application of miraculin as a taste-modifier to a chewing gum wherein miraculin is added to a chewing gum composition or a chewing gum composition is coated with miraculin.

Further Japanese Laid-Open No. 36214/1986 discloses an example of the application of miraculin as a taste-modifier to a mouth-wash composition wherein miraculin is added to a mouth-wash composition to thereby prevent a change in the taste of a juice taken after using the mouth-wash, which is caused by sodium lauryl sulfate remaining in the mouth.

It is further known that Curculigo latifolia fruits, which grow in Western Malaysia and the southern part of Thailand and belong to the genus Curculigo of Amaryllidaceae, are good to eat and exhibit an appetizing effect.

Although miraculin has such effects as described above, it has never been practically employed as a taste-modifier because of its poor stability. Thus neither any chewing gum composition containing miraculin nor any mouth-wash composition containing the same has been available in practice so far.

No effect of Curculigo latifolia fruits except the abovementioned one has been known so far.

SUMMARY OF THE INVENTION

It is the first object of the present invention to provide a novel and highly stable taste-modifier.

It is the second object of the present invention to provide a novel and highly stable taste-modifier for an acidic material, a material which is made acidic in the mouth or a material containing the same, which will be called a sour material hereinafter. The taste-modifier for a sour material of the present invention would exert a taste-modification effect when said sour material is taken.

It is the third object of the present invention to provide a chewing gum composition which exerts a novel taste-modification effect and has a stable taste-modification function.

It is the fourth object of the present invention to provide a mouth-wash composition which exerts a novel taste-modification effect and has a stable taste-modification function.

The present inventors have found that a sour material or water taken after eating Curculigo latifolia fruits would taste sweet. Thus they have attempted to identify the sweetness-inducer. As a result, they have found that a specific protein contained in Curculigo latifolia fruits is the aimed sweetness-inducer.

The present inventors have further found that a sour material taken following a Curculigo latifolia fruit would taste sweet, which suggests that said fruit may serve as a taste-modifier for a sour material for achieving the above object.

As a result of extensive studies, the present inventors have further found that a chewing gum achieving the above object can be obtained by adding fresh Curculigo latifolia fruits, dried fruits thereof or a curuculin-containing material obtained therefrom to a chewing gum composition.

As a result of extensive studies, the present inventors have further found that a mouth-wash achieving the above object can be obtained by adding fresh Curculigo latifolia fruits, dried fruits thereof or a curuculin-containing material obtained therefrom to a mouth-wash composition.

Accordingly, the present invention, which has been completed based on these findings, has succeeded in achieving the first object described above by providing a protein curuculin (the first invention) obtained by extracting from fresh Curculigo latifolia fruits or dried fruits thereof with an aqueous solution of a salt of a concentration of at least 0.01M.

The novel material curuculin according to the first invention has a high stability and is highly available as a taste-modifier. When the curuculin of the present invention or a material containing the same is taken followed by a sour material or water, said sour material or water would taste sweet. Namely, curuculin can impart a preferable sweetness to food products which should be sour from the viewpoint of, for example, storage stability or those which contain no sugar for clinical or nutritional reasons. Thus curuculin may be used for various purposes.

The present invention has succeeded in achieving the second object described above by providing a taste-modifier (the second invention) for a sour material comprising fresh Curculigo latifolia fruits, dried fruits thereof or a curuculin-containing material obtained therefrom.

The taste-modifier according to the second invention has a high stability. When the taste-modifier or a material containing the same is taken followed by a sour material, said sour material would taste sweet. Namely, the taste-modifier of the present invention can impart a preferable sweetness to food products which should be sour from the viewpoint of, for example, storage stability. Further the taste-modifier can give an enhanced sweetness to a food containing bitter, astringent or harsh components. Therefore it may be used for various purposes.

The present invention has further succeeded in achieving the third object described above by providing a chewing gum composition comprising fresh Curculigo latifolia fruits, dried fruits thereof or a curuculin-containing material obtained therefrom (the third invention).

The chewing gum composition according to the third invention exerts a novel taste-modification effect and has a stable taste-modification function. It would not only show a sustained chewing gum flavor but also make a sour material or water taken following the chewing gum sweet. Namely, the chewing gum composition relieves the sourness of the sour material and enhance the sweetness of the same to thereby make the sour material sweet and easy to take.

The present invention has furthermore succeeded in achieving the fourth object described above by providing a mouth-wash composition comprising fresh Curculigo latifolia fruits, dried fruits thereof or a curuculin-containing material obtained therefrom (the fourth invention).

The mouth-wash composition according to the fourth invention exerts a novel taste-modification effect and has a stable taste-modification function. It would sweeten not only the water to be taken together therewith but also a sour material or water taken following the same. When said mouth-wash composition contains sodium lauryl sulfate, it shows no undesirable aftertaste caused by the sodium lauryl sulfate.

DETAILED DESCRIPTION OF THE INVENTION

Now the protein curuculin, namely, the first invention will be described in detail.

The curuculin of the present invention may be obtained by extracting from fresh Curculigo latifolia fruits or dried fruits thereof with an aqueous solution of a salt of a concentration of at least 0.01M.

Examples of the salt include chlorides such as sodium chloride, potassium chloride, calcium chloride, magnesium chloride and ammonium chloride; phosphates such as sodium phosphate, potassium phosphate, magnesium phosphate and ammonium phosphate; carbonates such as sodium carbonate, potassium carbonate, magnesium carbonate and ammonium carbonate; sulfates such as sodium sulfates, magnesium sulfate, calcium sulfate and ammonium sulfate; sulfites such as sodium sulfite, magnesium sulfite, calcium sulfite and ammonium sulfite; nitrates such as sodium nitrate and potassium nitrate; nitrites such as sodium nitrite and potassium nitrite; lactates such as sodium lactate and calcium lactate; alum; burnt alum; sodium acetate; pyrophosphates such as sodium pyrophosphate and potassium pyrophosphate; propionates such as sodium propionate and calcium propionate; sodium benzoate; sodium fumarate; and sodium polyacrylate.

The method for drying Curculigo latifolia fruits is not particularly restricted. Namely, sun-dried Curculigo latifolia fruits, hot air-dried ones and lyophilized ones such as lyophilized pulp may be used in the present invention.

A typical example of the extraction of curuculin with the aqueous solution of a salt may be carried in the following manner.

An aqueous solution of a salt such as sodium chloride is added to fresh Curculigo latifolia fruits or dried fruits thereof and the obtained mixture is homogenized followed by filtering and centrifuging. Since curuculin is contained in the water-insoluble part of Curculigo latifolia sarcocarp, it is preferable to homogenize the above mixture of the fresh Curculigo latifolia fruits or dried fruits thereof and water followed by thoroughly washing the mixture to thereby remove the water-soluble part and extracting from the residue with the abovementioned salt solution so as to increase the purity of curuculin.

The concentration of the salt of the aqueous solution to be used for the extraction should be 0.01M or more, since curuculin can not be sufficiently extracted with a salt solution of a concentration lower than 0.01M. On the other hand, a salt solution of an excessively high concentration requires a prolonged period of time for desalting following the extraction. Thus the concentration of the salt solution preferably ranges from 0.1 to 1.0M, from the viewpoints of the extraction efficiency and the subsequent purification procedure.

The extract thus obtained with the use of the salt solution is then desalted and dried to thereby give a curuculin-containing material which is sufficiently available in practice. However the purity of curuculin can be further increased by purifying the above extract by ion exchange chromatography with the use of CM-Sepharose and HPLC with the use of a gel column followed by desalting and drying. Thus pure curuculin can be obtained. It is a matter of course that the curuculin purity may be further increased by various purification procedures other than those described above, for example, known protein purification procedures such as salting-out or solvent precipitation.

A typical example of the curuculin thus obtained is a protein having a molecular weight of approximately 12,500 dalton, an amino acid residue number of 97 and an iso-electric point of 7.1. This protein is present as a dimer of a molecular weight of approximately 26,000 dalton. The following Table 1 shows the amino acid composition of this protein. Thus it contains relatively large amounts of aspartic acid, leucine and glycine.

TABLE 1

| Amino acid | | Amino acid composition | |
|---|---|---|---|
| | | % by mol | No. of residues |
| Aspartic acid | (Asp) | 17.3 | 17 |
| Threonine | (Thr) | 6.4 | 6 |
| Serine | (Ser) | 7.0 | 7 |
| Glutamic acid | (Glu) | 7.2 | 7 |
| Proline | (Pro) | 1.2 | 1 |
| Glycine | (Gly) | 12.5 | 12 |
| Alanine | (Ala) | 5.3 | 5 |
| Cystine | (Half-cys) | — | — |
| Valine | (Val) | 6.8 | 7 |
| Methionine | (Met) | 0.4 | 1 |
| Isoleucine | (Ile) | 4.2 | 4 |
| Leucine | (Leu) | 14.5 | 14 |
| Tyrosine | (Tyr) | 5.2 | 5 |
| Phenylalanine | (Phe) | 1.3 | 1 |
| Lysine | (Lys) | 2.7 | 3 |
| Histidine | (His) | 2.4 | 2 |
| Arginine | (Arg) | 5.5 | 5 |
| Total | | | 97 |

The abovementioned protein curuculin of the present invention may be appropriately used as a taste-modifier.

The taste-modifier of the present invention comprising said curuculin may be either taken as such or appropriately added to, for example, foods, drinks or drugs. The amount of the taste-modifier to be added to, for example, a food may be appropriately determined depending on the purpose and use, based on the sweetness-induction activity of curuculin which will be shown hereinafter.

The food containing said taste-modifier comprising curuculin may be processed into various forms, for example, powder, solution, sheet, tablet, spray or emulsion, depending on the properties thereof.

(Function)

When taken before or together with a sour material, a nontaste material or water, the curuculin of the present invention would affect the receptor membrane on the tongue to thereby give a sweetness. When the curuculin of the present invention or a preparation containing the same is taken, therefore, a sour material, a nontaste material or water taken within 30 minutes thereafter would taste sweet.

Table 2 shows the sweetness-induction effects of pure curuculin on various aqueous solutions (curuculin concentration: $4 \times 10^{-5}$M). Table 2 shows that curuculin exerts a particularly high effect on a sour material.

TABLE 2

| Aqueous solution | Sweetness-induction effect |
| --- | --- |
| Citric acid (0.02 M) | Comparable to 0.3 M aqueous solution of sucrose |
| Ascorbic acid (0.02 M) | Comparable to 0.2 M aqueous solution of sucrose |
| Water | Comparable to 0.1 M aqueous solution of sucrose |
| Green tea (1 g/100 ml) | Comparable to 0.1 M aqueous solution of sucrose |
| Black tea (1 g/100 ml) | Comparable to 0.1 M aqueous solution of sucrose |

Different from miraculin contained in Synsepulm dulcificum fruits, the curuculin of the present invention remains stable in an aqueous solution. Thus curuculin or a preparation or a food containing the same may be readily processed not only into, for example, powder, tablets or sheet but also into solution, emulsion or spray.

The curuculin of the present invnetion per se has a slight sweetness.

Now the taste-modifier for a sour material according to the second invention will be described in detail.

The taste-modifier of the present invention may be obtained not only from fresh Curculigo latifolia fruits but also from dried ones. The dried Curculigo latifolia fruits may be obtained by any method without restriction. For example, sun-dried, hot air-dried or lyophilized ones, e.g., lyophilized pulp may be employed therefor.

The fresh Curculigo latifolia fruits or dried fruits thereof may be generally ground, milled or formed into a paste, though the present invention is not restricted thereby.

Alternately, the taste-modifier of the present invention may be a curuculin-containing material obtained from the abovementioned fresh Curculigo latifolia fruits or dried fruits thereof. Examples of said curuculin-containing material include curuculin extracted from said fresh Curculigo latifolia fruits or dried fruits thereof and a residue obtained by separating a curuculin-free component from appropriately treated fresh Curculigo latifolia fruits or dried fruits thereof. The abovementioned curuculin extracted from the fresh Curculigo latifolia fruits or dried fruits thereof may have any purity without restriction. Namely, either highly pure curuculin or a material containing curuculin together with a large amount of other components may be employed therefor. Similarly, the extract may contain other components.

The procedure for extracting the curuculin is not particularly restricted. The extraction process with the use of an aqueous solution of a salt of a concentration of at least 0.01M, namely the one shown in the above first invention, may be preferably employed.

The taste-modifier for a sour material of the present invention comprising said curuculin may be either taken as such or appropriately added to, for example, foods, drinks or drugs. The amount of the taste-modifier of the present invention to be added to, for example, a food may vary depending on the purpose and use. Generally it may be added in such an amount as to give 0.001 to 1 part by weight of curuculin to 100 parts by weight of a food.

The taste-modification effect of the taste-modifier of the present invention on a sour material may be further enhanced by adding bitter, astringent or harsh material(s) thereto. Namely, the taste-modifier of the present invention can give an elevated sweetness when a sour material is present in the mouth together with bitter, astringent or harsh material(s). It is not always required to take these bitter, astringent or harsh materials together with the sour material. Namely, they may be taken before or after taking the sour material in such a manner that they are present in the mouth together with the taste-modifier of the present invention and the sour material.

The food containing said taste-modifier comprising curuculin may be processed into various forms, for example, powder, solution, sheet, spray or emulsion, depending on the properties thereof.

(Function)

The taste-modifier of the present invention would affect the receptor membrane on the tongue in such a manner that a sour material taken thereafter would taste sweet. When the taste-modifier of the present invention or a preparation containing the same is taken, therefore, a sour material taken within 30 minutes thereafter would taste sweet.

The taste-modifier for a sour material of the present invention per se has a slight sweetness.

Now the chewing gum composition of the third invention will be described in detail.

The fresh Curculigo latifolia fruits, dried fruits thereof or a curuculin-containing material obtained therefrom contained in the chewing gum composition of the present invention have the following effects.

(1) Sustaining the taste of the chewing gum for a long time.

(2) Modifying the taste receptor on the tongue in such a manner as to impart a sweetness to a sour material or water taken following the chewing gum.

(3) Making it unnecessary to add conventionally used sugar or an artificial sweetener to the chewing gum for sustaining its taste, or significantly lowering the amount of such an additive as described above.

(4) Not only improving the taste of the chewing gum components and/or perfumes contained therein but also showing an excellent taste per se. This taste would be kept for an hour or longer, compared with the fact that a conventional chewing gum would lost its taste after being chewed for a few minutes.

(5) Improving the taste of a sour fruit perfume commonly contained in chewing gum compositions.

The fresh Curculigo latifolia fruits, dried fruits thereof or curuculin-containing material obtained therefrom to be used in the third invention may be those similar to the fresh Curculigo latifolia fruits, dried fruits thereof or curuculin-containing material obtained therefrom consisting the taste-modifier of the second invention.

The fresh Curculigo latifolia fruits, dried fruits thereof or curuculin-containing material obtained therefrom described above may be blended into a chewing gum composition by adding said fresh Curculigo latifolia fruits, dried fruits thereof or curuculin-containing material obtained therefrom to a chewing gum base; or coating a chewing gum composition comprising a chewing gum base with the fresh Curculigo latifolia fruits, dried fruits thereof or curuculin-containing material obtained therefrom. The latter process, i.e., coating is preferred to the former one, since it requires less amount of the fresh Curculigo latifolia fruits, dried fruits thereof or curuculin-containing material obtained therefrom in order to achieve an effect of improving or reinforcing the desired taste, than the former process does.

The coating may be effected by any method without limitation. For example, a Curculigo latifolia fruit powder may be dusted over a chewing gum or a chewing gum composition may be coated with Curculigo latifolia fruit paste.

A gum base suitable for the chewing gum composition of the present invention include unmodified Pontianak gum, glutacathyan, chicle, a gum latex base disclosed in U.S. Pat. No. 1,930,436, a jelutong base disclosed in U.S. Pat. No. 2,137,746, a mixture thereof and a paraffin-modified base.

The chewing gum composition of the present invention may preferably contain fresh Curculigo latifolia fruits, dried fruits thereof or a curuculin-containing material obtained therefrom in such an amount as to give at least 0.01 mg, preferably 0.1 to 1 mg, of curuculin per unit amount of the chewing gum, regardless of the form of the chewing gum. Although a larger amount of the fresh Curculigo latifolia fruits, dried fruits thereof or curuculin-containing material obtained therefrom may be used, it would cause substantially no advantage from the viewpoint of taste-modification.

The chewing gum composition of the present invention may further contain a mint or fruit perfume. Furthermore it may contain sugar, if desired.

In addition to the abovementioned components, the chewing gum composition of the present invention may contain a nontoxic acid which would reinforce the sweetness after the fresh Curculigo latifolia fruits, dried fruits thereof or curuculin-containing material obtained therefrom modified the taste receptor on the tongue. Thus the chewing gum product has an improved sweetness and a low caloric value. Examples of the nontoxic acid include carboxylic acids such as citric acid, malic acid, ascorbic acid, acetic acid and tartaric acid, inorganic acids at a low concentration and mixtures thereof. The acid may be used in such an amount as to give an effective molar concentration of 0.001 to 0.1M. Namely, the amount of acid included in the chewing gum composition is to be such an amount as to give the same sweetness as given by an aqueous solution of the acid of a concentration of 0.001 to 0.1M.

Curculigo latifolia fruits have a slight sweetness per se. Thus they may be simply added to a chewing gum base to thereby give a chewing gum of a fruity taste.

Now the mouth-wash composition according to the fourth invention will be described in detail.

The fresh Curculigo latifolia fruits, dried fruits thereof or curuculin-containing material obtained therefrom contained in the mouth-wash composition of the present invention have the following effects.

(1) Modifying the taste receptor on the tongue after using the mouth-wash composition. Thus the water taken thereafter for rinsing the mouth tastes sweet.

(2) Imparting a sweetness to a sour material which is taken after using the mouth-wash composition.

(3) When the mouth-wash composition contains sodium lauryl sulfate, the deterioration of the taste of a food, which is taken after using the mouth-wash composition, caused by the sodium lauryl sulfate remaining in the mouth can be prevented. Further a preferable sweetness is imparted to said food.

(4) A mouth-wash composition for children can be obtained, without using any specific seasoning for children, by adding fresh Curculigo latifolia fruits, dried fruits thereof or a curuculin-containing material obtained therefrom thereto.

The mouth-wash composition of the present invention, which comprises fresh Curculigo latifolia fruits, dried fruits thereof or a curuculin-containing material obtained therefrom, may be processed into, for example, mouth-wash agent, liquid mouth-refreshing agent, tooth liquid and toothpaste.

The fresh Curculigo latifolia fruits, dried fruits thereof or curuculin-containing material obtained therefrom to be used in the fourth invention may be the same as those which are used in the third invention.

The fresh Curculigo latifolia fruits, dried fruits thereof or curuculin-containing material obtained therefrom may be added to the mouth-wash composition by any method without restriction. For example, they may be added thereto as such. Alternately, the fresh Curculigo latifolia fruits, dried fruits thereof or curuculin-containing material obtained therefrom may be stabilized by encapsulating or coating with, for example, dextran.

The fresh Curculigo latifolia fruits, dried fruits thereof or curuculin-containing material obtained therefrom may be used in such an amount as to give a curuculin content of 1 to $10^{-3}$% (by weight, the same will apply hereinafter), preferably $10^{-1}$ to $10^{-2}$%, based on the total composition. Although a larger amount of fresh Curculigo latifolia fruits, dried fruits thereof or curuculin-containing material obtained therefrom may be used, it would give substantially no advantage from the viewpoint of taste-modification.

The mouth-wash composition of the present invention may further contain various components depending on its form.

For example, a liquid composition such as a mouth-wash liquor may comprise a solvent such as water or ethanol; a thickner such as polyethylene glycol, sorbitol, glycerol or propylene glycol; a water-soluble salt of an alkyl sulfate carrying 8 to 16 carbon atoms such as sodium lauryl sulfate; a surfactant such as sodium dodecylbenzenesulfonate, sodium hydrogenated coconut fatty acid monoglyceride monosulfate, sodium lauryl sulfoacetate, sodium lauroyl sarcosinate, N-acyl glutamate, lauryl diethanolamide or sucrose fatty acid esters; an essential oil such as peppermint oil or spearmint oil; a perfume such as l-menthol, carvone, eugenol or anethole; a sweetener such as saccharin sodium, stevioside, neohesperidindihydrochalcone, glycyrrhizin, perillartine or p-methoxycinnamic aldehyde; and a preservative.

When the mouth-wash is in the form of a gel or a paste, on the other hand, it may comprise a binder such as carboxymethyl cellulose sodium, hydroxyethyl cellulose, alginates, carrageenan, gum arabic or polyvinyl alcohol. A mouth-wash composition in the form of a toothpaste may comprise a sanding agent such as dibasic calcium phosphate, calcium carbonate, calcium pyrophosphate, insoluble sodium metaphosphate, amorphous silica, crystalline silica, alumino silicate, aluminum oxide, aluminum hydroxide or a resin.

The mouth-wash composition of the present invention may further contain an active ingredient such as chlorohexidine, dextranase, mutanase, sorbic acid, alexidine, hinokitiol, cetylpyrimidium chloride, an alkylglycine, an alkyldiamino-ethylglycine salt, allantoin, 1-aminocaproic acid, tranexamic acid, azulene, vitamin E, a water-soluble monobasic or dibasic phosphate, a quaternary ammonium compound, sodium chloride or a herb extract.

The mouth-wash composition of the present invention may be prepared in a known manner depending on the type.

To further illustrate the present invention, the following Examples will be given.

EXAMPLE 1

To 30 g of lyophilized Curculigo latifolia fruit pulp, was added 600 ml of water. The obtained mixture was homogenized in a mixer for two minutes and then centrifuged at 10,000 rpm for 30 minutes. After removing the colored supernatant, 600 ml of water was added to the residue. The obtained mixture was homogenized and centrifuged followed by removing the supernatant. This procedure was repeated four times until the supernatant was not colored any more.

To the residue thus obtained, was added 250 ml of a 0.5M aqueous solution of NaCl. The resulting mixture was homogenized in a mixer for two minutes and then filtered under reduced pressure. After collecting the filtrate, 250 ml of the 0.5M aqueous solution of NaCl was further added to the residue. The mixture was homogenized and filtered under reduced pressure. Then the filtrate was collected.

These filtrates were combined and centrifuged at 30,000 rpm for one hour to thereby give a crude curuculin extract as the supernatant.

This crude extract was desalted and lyophilized. Thus a curuculin-containing material, i.e., crude curuculin was obtained.

EXAMPLE 2

500 ml of the crude curuculin extract obtained in the above Example 1 was concentrated to 30 ml by ultrafiltration. Then 70 ml of a 0.01M phosphate buffer (pH 6.8) was added thereto to thereby give a total volume of 100 ml. The mixture thus obtained was employed as a sample. The sample was subjected to CM-SEPHAROSE (trade name) column chromatography with the use of a CM-SEPHAROSE CL-6B column (bed volume: 130 ml, bed height: 17 cm) which had been equilibrated with a 0.01M phosphate buffer (pH 6.8). After washing with a 0.01M phosphate buffer (pH 6.8), the column was subjected to gradient elution with the use of 0–1.0M NaCl/0.01M phosphate buffer solution (pH 6.8) and an active fraction was collected.

The active fraction was desalted and lyophilized to thereby give a curuculin-containing material, i.e., crude curuculin.

EXAMPLE 3

The active fraction obtained in the above Example 2 was concentrated by ultrafiltration and subjected to HPLC with the use of a gel column (TSK Gel G3000SW (trade name); mfd. by Toyo Soda Mfg. Co.). A 0.01M phosphate buffer solution (pH 6.8) was employed as an eluent.

Thus curuculin was eluted as a highly active fraction showing a sharp peak.

This active fraction was desalted and lyophilized to thereby give purified curuculin.

The purified curuculin thus obtained was subjected to SDS-PAGE in the presence of 8.0M of urea. As a result, it showed a single band corresponding to a molecular weight of 12,500 dalton, which indicated that it was a pure compound.

Table 3 shows the protein content, activity yield and specific activity, each per 30 g of the starting lyophilized Curculigo latifolia pulp, of each product obtained above.

TABLE 3

|  | Protein content | Activity yield | Specific activity |
| --- | --- | --- | --- |
| Lyophilized pulp | 30 g | 100 | 1 |
| Ex. 1 | 38 mg | 85.4 | 672 |
| Ex. 2 | 11.5 mg | 73.6 | 1920 |
| Ex. 3 | 10 mg | 66.7 | 2000 |

EXAMPLE 4

10 mg of the crude curuculin obtained in the above Example 1 and 1 mg of sodium chloride were dissolved in 20 ml of water to thereby give a 0.05% aqueous solution of the crude curuculin. This solution remained stable after allowing to stand at room temperature (around 25° C.) for one month. 1 ml of this solution was kept in the mount for one minute and then evaporated. Subsequently 0.02M citric acid, water and black tea were taken independently. Table 4 shows the sweetness thus shown by each drink.

TABLE 4

| Drink | Sweetness |
| --- | --- |
| 0.02 M citric acid | Comparable to 10% aqueous solution of sugar |
| Water | Comparable to 3% aqueous solution of sugar |
| Black tea | Comparable to 2% aqueous solution of sugar |

Thus the black tea tasted as sweet as a common one containing sugar.

EXAMPLE 5

A black coffee jelly (A) and a sugar-containing one (B), each having the following composition, were prepared.

TABLE 5

|  | A (%) | B (%) |
| --- | --- | --- |
| Refined white sugar | — | 4 |
| Coffee extract | 2 | 2 |
| Concentrated coffee | 8 | 8 |
| Caramel | 0.1 | 0.1 |
| Gelatin | 2 | 2 |
| Caramel bitter base | 0.5 | 0.5 |
| Water | 87.4 | 83.4 |

Separately, 0.005% of the crude curuculin obtained in the above example 1 was added to a commercially available fresh cream (C) to thereby give a curuculin-containing fresh cream (D).

The components of the coffee jelly (A) were dissolved in the water, poured into a cup and solidified by cooling. Approximately 10 g of the fresh cream (D), which had been whipped with 10% of sugar, was pressed thereon to thereby give a cream coffee jelly. Similarly, the fresh cream (C), which had been whipped with 10% of sugar, was pressed on the coffee jelly (B) to thereby give another cream coffee jelly.

The taste of the coffee jelly (A) taken following the whipped cream (D) was similar to that of the coffee jelly (B) taken following the whipped cream (C).

EXAMPLE 6

The coffee jelly (A) prepared in the above Example 5 was coated with 0.2 g of an edible film containing 0.2% of the crude curuculin obtained in Example 1 to thereby prevent the jelly from drying. The tase of the coffee jelly taken following the edible film was similar to that of the coffee jelly (B) described in Example 5.

EXAMPLE 7

To 30 g of hot air-dried Curculigo latifolia fruits, was added 600 ml of water. The obtained mixture was homogenized in a mixer for two minutes and then centrifuged at 10,000 rpm for 30 minutes. After removing the colored supernatant, 600 ml of water was added to the residue. The mixture was homogenized and centrifuged followed by removing the supernatant. This procedure was repeated four times until the supernatant was not colored any more.

To the obtained residue, was added 250 ml of a 0.5M aqueous solution of NaCl. This mixture was homogenized in a mixer for two minutes and then filtered under reduced pressure. After collecting the filtrate, 250 ml of a 0.5M aqueous solution of NaCl was further added to the residue. The obtained mixture was homogenized and filtered under reduced pressure and the filtrate was collected.

These filtrates were combined and centrifuged at 30,000 rpm for one hour. Thus a crude curuculin extract was obtained as the supernatant.

This crude extract was desalted and dried to thereby give a curuculin-containing material, i.e., curde curuculin.

EXAMPLE 8

500 ml of the crude curuculin extract obtained in the above Example 7 was concentrated to 30 ml by ultrafiltration. 70 ml of a 0.01M phosphate buffer solution (pH 6.8) was added thereto to thereby give a total volume of 100 ml. The mixture thus obtained was employed as a sample. This sample was subjected to CM-SEPHAROSE column chromatography with the use of a CM-SEPHAROSE CL-6B column (bed volume: 130 ml, bed height: 17 cm) which had been equilibrated with a 0.01M phosphate buffer solution (pH 6.8). After washing with a 0.01M phosphate buffer solution (pH 6.8), the column was subjected to gradient elution with the use of 0-1.-M NaCl/0.01M phosphate buffer solution (pH 6.8) and an active fraction was collected.

This active fraction was desalted and dried to thereby give a curuculin-containing material, i.e., crude curuculin.

EXAMPLE 9

The active fraction obtained in the above Example 8 was concentrated by ultrafiltration and subjected to HPLC with the use of a gel column (TSK Gel G3000SW (trade name); mfd. by Toyo Soda Mfg. co.). A 0.01M phosphate buffer solution (pH 6.8) was employed as a eluent.

Thus curuculin was eluted as a highly active fraction showing a sharp peak.

This active fraction was desalted and lyophilized to thereby give purified curuculin.

The purified curuculin thus obtained was subjected to SDS-PAGE in the presence of 8.0M of urea. As a result, it showed a single band corresponding to a molecular weight of 12,500 dalton, which indicated that it was a pure compound.

Table 6 shows the protein content, activity yield and specific activity, each per 30 g of the starting dried Curculigo latifolia fruits, of each product obtained above.

TABLE 6

|  | Protein content | Activity yield | Specific activity |
| --- | --- | --- | --- |
| Dried fruits | 30 g | 100 | 1 |
| Ex. 7 | 38 mg | 85.4 | 672 |
| Ex. 8 | 11.5 mg | 73.6 | 1920 |
| Ex. 9 | 10 mg | 66.7 | 2000 |

EXAMPLE 10

100 mg of the crude curuculin obtained in the above Example 7 and 1 mg of sodium chloride were dissolved in 20 ml of water to thereby give a 0.5% aqueous solution of the crude curuculin. This solution remained stable after allowing to stand at room temperature (around 25° C.) for one month. 1 ml of this solution was kept in the mouth for one minute and then expectorated. Subsequently 0.02M citric acid, water and black tea were taken independently. Table 7 shows the sweetness thus shown by each drink.

TABLE 7

| Drink | Sweetness |
| --- | --- |
| 0.02 M citric acid | Comparable to 10% aqueous solution of sugar |
| Water | Comparable to 3% aqueous solution of sugar |
| Black tea | Comparable to 2% aqueous solution of sugar |

Thus the black tea tasted as sweet as a common one containing sugar.

EXAMPLE 11

A black coffee jelly (A) and a sugar-containing one (B), each having the following composition, were prepared.

TABLE 8

|  | A (%) | B (%) |
| --- | --- | --- |
| Refined white sugar | — | 4 |
| Coffee extract | 2 | 2 |
| Concentrated coffee | 8 | 8 |
| Caramel | 0.1 | 0.1 |
| Gelatin | 2 | 2 |
| Caramel bitter base | 0.5 | 0.5 |
| Water | 87.4 | 83.4 |

Separately, 0.05% of the crude curuculin obtained in the above Example 7 was added to a commercially available fresh cream (C) to thereby give a curuculin-containing fresh cream (D).

The components of the coffee jelly (A) were dissolved in the water, poured into a cup and solidified by cooling. Approximately 10 g of the fresh cream (D), which had been whipped with 10% of sugar, was pressed thereon to thereby give a cream coffee jelly. Similarly, the fresh cream (C), which had been whipped with 10% of sugar, was pressed on the coffee jelly (B) to thereby give another cream coffee jelly.

The taste of the coffee jelly (A) taken following the whipped cream (D) was similar to that of the coffee jelly (B) taken following the whipped cream (C).

EXAMPLE 12

The coffee jelly (A) prepared in the above Example 11 was coated with 0.2 g of an edible film containing 0.2% of the crude curuculin obtained in Example 7 to thereby prevent the jelly from drying. The taste of the coffee jelly taken following the edible film was similar to that of the coffee jelly (B) described in Example 11.

EXAMPLES 13 TO 18

The procedure of Example 7 was repeated except that the 0.5M aqueous solution of NaCl was substituted with a 0.5M aqueous solution of KCl (Example 13), a 0.5M aqueous solution of $CaCl_2$ (Example 14), a 0.5M aqueous solution of $NaHCO_3$ (Example 15), a 0.5M aqueous solution of $MgCO_3$ (Example 16), a 0.2M aqueous solution of $KH_2PO_4$ (Example 17) or a 0.2M aqueous solution of $NaH_2PO_4$ (Example 18). Thus a curuculin-containing material, i.e., crude curuculin was obtained in each case.

EXAMPLE 19

1 g of a Curculigo latifolia fruit was ground in a mortar to thereby give a sample of the taste-modifier of the present invention in the form of a paste. 0.5 g of this pasty sample was kept in the mouth in such a manner that it come in contact with the whole upper surface of the tongue. One minute thereafter, 100 ml of lemon juice was kept in the mouth. Thus a sweetness was imparted to the lemon juice and, therefore, the lemon juice tasted as sweet as an orange.

EXAMPLE 20

Curculigo latifolia fruits were peeled and their seeds were removed. The Curculigo latifolia sarcocarp thus obtained was dried at 40° C. for 24 hours and then ground in a mixer for two minutes. Thus a sample of the taste-modifier of the present invention in the form of a powder was obtained. 0.2 g of this powdery sample was kept in the mouth in such a manner that it came into contact with the whole upper surface of the tongue. One minute thereafter, 0.5 g of a 1-ascorbic acid powder was kept in the mouth. Thus a sweetness was imparted to the ascorbic acid. Namely, the sourness of the ascorbic acid was masked and thus it showed a refreshing sweet and sour taste.

EXAMPLE 21

A mixture of 0.9 g of the powdery sample obtained in the above Example 20 and 0.1 g of a citric acid powder was kept in the mouth. Thus it showed a preferable sweet and sour taste.

EXAMPLE 22

To 20 kg of Curculigo latifolia sarcocarp, was added 100 l of water. The obtained mixtrue was homogenized and centrifuged at 10,000 rpm for 30 minutes. After removing the supernatant, 100 l of water was further added to the residue. The mixture was homogenized and centrifuged again followed by removing the supernatant.

To the residue thus obtained, was added 30 l of a 0.5M aqueous solution of NaCl. The mixture was homogenized in a mixer for two minutes and filtered under reduced pressure. After collecting the filtrate, 30 l of the aqueous solution of NaCl was further added to the residue. The obtained mixture was homogenized and filtered under reduced pressure again followed by collecting the filtrate.

These filtrates were combined and centrifuged at 30,000 rpm for an hour. Thus a crude curuculin extract was obtained as the supernatant.

This crude extract was desalted by ultrafiltration and lyophilized to thereby give a curuculin-containing material.

A coffee drink of the following composition was prepared with the use of the curuculin-containing material obtained above. This coffee drink was pasteurized at 140° C. for three seconds with a VTIS pasteurizer (mfd. by Alfa Laval Co.) and then aseptically packed in a container to thereby give a sugar-free coffee drink product.

| Composition: | (%) |
| --- | --- |
| coffee extract | 2 |
| concentrated coffee | 8 |
| caramel | 0.1 |
| caramel bitter base | 0.5 |
| curuculin-containing material | 0.5 |
| water | 88.9. |

This sugar-free coffee drink tasted no bitterness but an improved sweetness, compared with the taste of a sour material taken alone.

EXAMPLE 23

A lemon-flavored chewing gum of the following composition was prepared in the following manner.

| Composition: | (g) |
| --- | --- |
| chicle gum | 130.00 |
| paraffin wax | 37.00 |
| Tolu balsam | 6.50 |
| Peruvian balsam | 3.00 |
| citric acid | 55.00 |
| sodium chloride | 5.00 |
| water | 170.00 |
| synthetic colorant (yellow) | 1.00 |
| synthetic lemon flavor | 10.00 |

The above materials werer mixed together in a mixer under stirring at 90° C. for 20 minutes. The obtained chewing gum composition was then molded into bars. Each chewing gum bar thus obtained was coated with approximately 20 to 30 mg of a powder obtained by drying Curculigo latifolia fruits and powdering the same.

The lemon-flavored chewing gum thus prepared sustained its sweet taste in the mouth for a prolonged period of time, though it contained no sugar. Further a lemon taken following this chewing gum tasted as sweet as an orange.

EXAMPLE 24

Curculigo latifolia fruits were peeled and their seeds were removed. The Curculigo latifolia sarcocarp thus obtained was dried at 40° C. for 24 hours and ground in a mixer for two minutes to thereby give a powder. A toothpaste of the following composition was prepared by using this Curculigo latifolia sarcocarp powder.

| Composition: | (%) |
|---|---|
| dibasic calcium phosphate | 45.0 |
| carboxymethyl cellulose dodium | 0.8 |
| sorbitol | 15.0 |
| propylene glycol | 3.0 |
| silica gel | 3.0 |
| sodium lauryl sulfate | 1.5 |
| perfume | 1.0 |
| Curculigo latifolia powder | 2.0 |
| water | balance |
| Total | 100.0 |

The toothpaste thus obtained per se tasted sweet and further sweetened the gargle water taken thereafter. Furthermore a lemon taken following the toothpaste tasted as sweet as an orange.

EXAMPLE 25

Curculigo latifolia fruits were peeled and their seeds were removed. 30 g of the sarcocarp thus obtained was ground in a mortar and 100 ml of water was added thereto. Then the mixture was homogenized in a mixer for two minutes and centrifuged at 10,000 rpm for 30 minutes. After removing the supernatant, 100 ml of water was added to the residue. The resulting mixture was then homogenized and centrifuged again followed by removing the supernatant. With the use of the residue thus obtained, a mouth-wash of the following composition was prepared.

| Composition: | (%) |
|---|---|
| ethyl alcohol (90%) | 20.0 |
| sodium lauroyl sarcosinate | 0.5 |
| perfume | 1.0 |
| sodium monofluorophosphate | 0.15 |
| disodium phosphate | 0.3 |
| monosodium phosphate | 0.7 |
| Curculigo latifolia product | 0.5 |

| Composition: | (%) |
|---|---|
| water | balance |
| Total | 100.0 |

A sugar-free coffee taken after using the mouth-wash thus obtained showed a sufficient sweetness.

What is claimed is:

1. A protein curuculin obtained by extraction from fresh Curculigo latifolia fruits or dried fruits thereof with an aqueous solution of a salt of a concentration of at least 0.01 M.

2. A taste-modifier comprising the curuculin of claim 1.

3. A food, a drink or drug which contains a taste-modifier comprising the curuculin of claim 1.

4. The food, drink or drug as set forth in claim 3, which is processed into a powder, a solution, a sheet, a tablet, a spray or an emulsion.

5. A process for obtaining a protein curuculin which comprises extracting fresh Curculigo latifolia fruits or dried fruits thereof with an aqueous solution of a salt of a concentration of at least 0.01 M.

6. A taste-modifier for a sour material which comprises the curuculin of claim 1.

7. The taste-modifier for a sour material as set forth in claim 6, mixed with bitter, astringent and/or harsh component(s).

8. The food, drink or drug of claim 3, containing 0.001 to 1 part by weight curuculin to 100 parts by weight food, drink or drug.

9. The chewing-gum composition containing 0.1 to 1 mg of curuculin per unit amount of the composition.

10. The process as set forth in claim 5, wherein fresh Curculigo latifolia fruits or dried fruits thereof are washed prior to extracting said fresh Curculigo latifolia fruits or dried fruits thereof with an aqueous solution of a salt to thereby remove the water-soluble part.

11. A mouthwash composition containing the curuculin of claim 1.

* * * * *